United States Patent
Baik et al.

(10) Patent No.: US 10,136,854 B2
(45) Date of Patent: Nov. 27, 2018

(54) STRETCHABLE THERMOELECTRIC MATERIAL AND THERMOELECTRIC DEVICE INCLUDING THE SAME

(71) Applicant: Samsung Electronics Co., Ltd., Suwon-si, Gyeonggi-do (KR)

(72) Inventors: Seunghyun Baik, Seoul (KR); Daewoo Suh, Seoul (KR); Dongmok Lee, Suwon-si (KR); Sanghoon Lee, Suwon-si (KR)

(73) Assignees: Samsung Electronics Co., Ltd., Gyeonggi-Do (KR); Research & Business Foundation Sungkyunkwan University, Gyeonggi-Do (KR)

(*) Notice: Subject to any disclaimer, the term of this patent is extended or adjusted under 35 U.S.C. 154(b) by 36 days.

(21) Appl. No.: 14/724,220

(22) Filed: May 28, 2015

(65) Prior Publication Data

US 2015/0342523 A1 Dec. 3, 2015

(30) Foreign Application Priority Data

May 30, 2014 (KR) .................. 10-2014-0066523

(51) Int. Cl.
*H01L 35/30* (2006.01)
*A61B 5/00* (2006.01)
*H01L 35/32* (2006.01)
(Continued)

(52) U.S. Cl.
CPC .......... *A61B 5/6801* (2013.01); *A61B 5/1118* (2013.01); *A61B 5/6802* (2013.01); *A61B 5/6831* (2013.01); *H01L 35/16* (2013.01); *H01L 35/18* (2013.01); *H01L 35/20* (2013.01); *H01L 35/22* (2013.01); *H01L 35/24* (2013.01); *H01L 35/26* (2013.01); *H01L 35/32* (2013.01); *H02J 7/355* (2013.01); *A61B 2560/0219* (2013.01); *A61B 2562/0276* (2013.01); *A61B 2562/12* (2013.01)

(58) Field of Classification Search
CPC ................ H01L 35/00–35/34; H01L 27/16
USPC ................................. 136/200–242
See application file for complete search history.

(56) References Cited

U.S. PATENT DOCUMENTS

2005/0059307 A1* 3/2005 Moeseke ............ A41D 31/0061
442/134
2006/0051677 A1* 3/2006 Matsushima .......... C25D 17/10
429/235
(Continued)

FOREIGN PATENT DOCUMENTS

JP 2010192780 * 9/2010
JP 2014-029932 A 2/2014
(Continued)

OTHER PUBLICATIONS

Korean Office Action dated Jul. 30, 2015 issued in corresponding Korean Application No. 10-2014-0066523 (full English translation provided).

*Primary Examiner* — Bach T Dinh
(74) *Attorney, Agent, or Firm* — Harness, Dickey & Pierce, P.L.C.

(57) ABSTRACT

A thermoelectric material includes a stretchable polymer, and a thermoelectric structure and an electrically conductive material that are mixed together with the stretchable polymer. The thermoelectric material may be applied to self-power generating wearable electronic apparatuses.

8 Claims, 11 Drawing Sheets

(51) Int. Cl.
*H01L 35/16* (2006.01)
*H01L 35/18* (2006.01)
*H01L 35/22* (2006.01)
*H01L 35/20* (2006.01)
*A61B 5/11* (2006.01)
*H02J 7/35* (2006.01)
*H01L 35/24* (2006.01)
*H01L 35/26* (2006.01)

(56) References Cited

U.S. PATENT DOCUMENTS

| | | | | |
|---|---|---|---|---|
| 2008/0121263 A1* | 5/2008 | Schutte | ............... | H01L 35/32 |
| | | | | 136/203 |
| 2009/0044848 A1* | 2/2009 | Lashmore | ............... | H01L 35/22 |
| | | | | 136/201 |
| 2010/0098957 A1* | 4/2010 | Park | ............... | B32B 7/02 |
| | | | | 428/457 |
| 2010/0319750 A1* | 12/2010 | Meng | ............... | B82Y 30/00 |
| | | | | 136/239 |
| 2011/0163636 A1* | 7/2011 | Sirbuly | ............... | B82Y 30/00 |
| | | | | 310/339 |
| 2012/0018682 A1* | 1/2012 | Minami | ............... | H01L 35/26 |
| | | | | 252/514 |
| 2012/0024333 A1* | 2/2012 | Lee | ............... | C04B 35/547 |
| | | | | 136/205 |
| 2012/0114961 A1* | 5/2012 | Lee | ............... | H01L 35/16 |
| | | | | 428/570 |
| 2012/0148764 A1* | 6/2012 | Navone | ............... | B41M 5/0011 |
| | | | | 427/600 |
| 2013/0252234 A1* | 9/2013 | Nassef | ............... | B01L 3/502707 |
| | | | | 435/5 |
| 2013/0312806 A1* | 11/2013 | Carroll | ............... | B82Y 30/00 |
| | | | | 136/212 |

FOREIGN PATENT DOCUMENTS

| | | | |
|---|---|---|---|
| KR | 20110086047 A | | 7/2011 |
| KR | 10-1068964 B1 | | 9/2011 |
| KR | 101144888 | * | 3/2012 |
| KR | 20120020582 A | | 3/2012 |
| KR | 20120027206 A | | 3/2012 |
| KR | 20120029864 A | | 3/2012 |
| KR | 10-1144888 B1 | | 5/2012 |
| KR | 10-1346568 B1 | | 1/2014 |

* cited by examiner

STRETCHABLE THERMOELECTRIC MATERIAL AND THERMOELECTRIC DEVICE INCLUDING THE SAME

RELATED APPLICATION

This application claims priority under 35 U.S.C. § 119 to Korean Patent Application No. 10-2014-0066523, filed on May 30, 2014, in the Korean Intellectual Property Office, the disclosure of which is incorporated herein in its entirety by reference.

BACKGROUND

1. Field

The present disclosure relates to a stretchable thermoelectric material and/or a thermoelectric device including the stretchable thermoelectric material.

2. Description of Related Art

Thermoelectric conversion is the conversion of thermal energy to electric energy and vice versa. The Peltier effect refers to an effect in which a temperature difference is generated between both ends of a thermoelectric material when a current flows through the thermoelectric material, and the Seebeck effect refers to an reverse effect in which electricity is generated when there is a temperature difference between both ends of a thermoelectric material.

Cooling systems operating by the Peltier effect may be effective to use in some applications where it may be difficult to use existing cooling systems such as passive cooling systems or refrigerant gas compression type cooling systems. Thermoelectric cooling is an eco-friendly cooling technique which does not use refrigerant gas, thereby limiting and/or preventing any environmental problems. If the efficiency of thermoelectric cooling is improved by the development of highly efficient thermoelectric cooling materials, the application field thereof may be expanded to general-purpose cooling apparatuses such as refrigerators and air conditioners.

In addition, the Seebeck effect may be used to produce electric energy from heat generated by computers, automobile engines, industrial plants, etc. Thermoelectric power generated by the Seebeck effect may become a new renewable energy source. Along with the increasing interest in new energy sources, the environment, the reuse of waste energy, etc., the interest in thermoelectric devices has increased.

There is an increasing interest in polymer thermoelectric materials or flexible thermoelectric materials for large-area thermoelectric devices or wearable thermoelectric apparatuses.

As compared with thermoelectric inorganic materials, polymer thermoelectric materials or flexible thermoelectric materials are non-toxic and inexpensive, and it is easy to manufacture large-area thermoelectric devices using polymer thermoelectric materials or flexible thermoelectric materials. In general, however, the thermoelectric conversion efficiency of polymer thermoelectric materials or flexible thermoelectric materials is low.

SUMMARY

Provided is a thermoelectric material having stretchability and high thermoelectric conversion efficiency.

Provided is a thermoelectric device including the thermoelectric material and applicable to wearable electronic apparatuses.

Additional aspects will be set forth in part in the description which follows and, in part, will be apparent from the description, or may be learned by practice of example embodiments.

According to example embodiments, a thermoelectric material includes a stretchable polymer, and a thermoelectric structure and an electrically conductive material that are mixed together with the stretchable polymer.

In example embodiments, the stretchable polymer may include at least one of poly(styrene-isoprene-styrene) (SIS), poly(styrene-butadiene-styrene) (SBS), poly(styrene-ethylene/butylene-styrene) (SEBS), polyvinylidenefluoride (PVDF), nitrile butadiene rubber (NBR), polyurethane (PU), poly(dimetylsiloxane) (PDMS), polyurethane acrylate (PUA), perfluoropolyether (PFPE), polyester (PE), polybutadiene (PB), and polyisoprene.

In example embodiments, the thermoelectric structure may include at least one of an Sb—Te-containing material, a Bi—Te-containing material, a Bi—Sb—Te-containing material, a Co—Sb-containing material, a Pb—Te-containing material, a Ge—Tb-containing material, a Si—Ge-containing material, a Sm—Co-containing material, and a carbon-containing material.

In example embodiments, the carbon-containing material may include at least one of carbon nanotubes, graphene, and graphite.

In example embodiments, the electrically conductive material may include at least one of a carbon nanomaterial and a metallic material.

In example embodiments, the carbon nanomaterial may include at least one of carbon nanotubes, graphene, and graphene nanoparticles.

In example embodiments, the electrically conductive material may include the carbon nanotubes and the metallic material. The metallic material may be metal nanoparticles. The metal nanoparticles may be adsorbed on surfaces of the carbon nanotubes.

In example embodiments, the metallic material may include gold (Au), silver (Ag), platinum (Pt), copper (Cu), nickel (Ni), aluminum (Al), palladium (Pd), rhodium (Rh), and ruthenium (Ru).

In example embodiments, the thermoelectric structure and the electrically conductive material mixed together may be carbon nanotubes and metal nanoparticles. The metal nanoparticles may be adsorbed on surfaces of the carbon nanotubes.

In example embodiments, the thermoelectric structure and the electrically conductive material may include carbon nanotubes.

In example embodiments, the carbon nanotubes may be a multi-walled carbon nanotube (MWCNT) array. The carbon nanotubes may be arranged in a direction.

In example embodiments, the multi-walled carbon nanotube array may be embedded in the stretchable polymer.

In example embodiments, the stretchable polymer may have uniaxial stretchability. A length of the carbon nanotubes in the multi-walled carbon nanotube array may be parallel to a stretching direction of the stretchable polymer.

In example embodiments, the stretchable polymer may have uniaxial stretchability. A length of the carbon nanotubes in the multi-walled carbon nanotube array may be perpendicular to a stretching direction of the stretchable polymer. According to example embodiments, a thermoelectric device may include the thermoelectric material, and first and second electrodes electrically connected to respective ends of the thermoelectric material.

In example embodiments, the thermoelectric device may further include an electronic device electrically connected to the first and second electrodes.

In example embodiments, the electronic device may be one of a power consuming device, a power storage device, and a power supply device.

According to example embodiments, a wearable electronic apparatus may be configured to be put on an object for inspecting the object. The wearable electronic apparatus may include the thermoelectric material, first and second electrodes electrically connected to respective ends of the thermoelectric material, a power storage device connected to the first and second electrodes, and an operation unit. The power storage device may be configured to store electric energy generated in the thermoelectric material based on a temperature difference between both the ends of the thermoelectric material. The temperature difference may be caused by heat provided by the object. The operation unit may be configured to receive the electric energy from the power storage device and to perform an inspection operation on the object.

In example embodiments, the operation unit may be configured to measure a health or motion status of the object.

According to example embodiments, an electronic apparatus includes the thermoelectric material, first and second electrodes electrically connected to respective ends of the thermoelectric material, and a power supply device connected to the first and second electrodes. The power supply device is configured to apply a current to the thermoelectric material for forming a hot spot cooling region at one of the respective ends of the thermoelectric material.

According to example embodiments, a thermoelectric material includes a stretchable polymer, a thermoelectric structure mixed in the stretchable polymer, and an electrically conductive material mixed in the stretchable polymer. The thermoelectric material contains carbon.

In example embodiments, the stretchable polymer may include at least one of poly(styrene-isoprene-styrene) (SIS), poly(styrene-butadiene-styrene) (SBS), poly(styrene-ethylene/butylene-styrene) (SEBS), polyvinylidenefluoride (PVDF), nitrile butadiene rubber (NBR), polyurethane (PU), poly(dimetylsiloxane) (PDMS), polyurethane acrylate (PUA), perfluoropolyether (PFPE), polyester (PE), polybutadiene (PB), and polyisoprene.

In example embodiments, the electrically conductive material may include metal nanoparticles.

In example embodiments, the thermoelectric structure may include carbon nanotubes embedded in the stretchable polymer. The metal nanoparticles may be adsorbed on the carbon nanotubes.

In example embodiments, the carbon nanotubes may be arranged in an array and lengths of the carbon nanotubes may be parallel to each other.

BRIEF DESCRIPTION OF THE DRAWINGS

The foregoing and other features of inventive concepts will be apparent from the more particular description of non-limiting embodiments of inventive concepts, as illustrated in the accompanying drawings in which like reference characters refer to like parts throughout the different views. The drawings are not necessarily to scale, emphasis instead being placed upon illustrating principles of inventive concepts. In the drawings.

DETAILED DESCRIPTION

Figure 1:
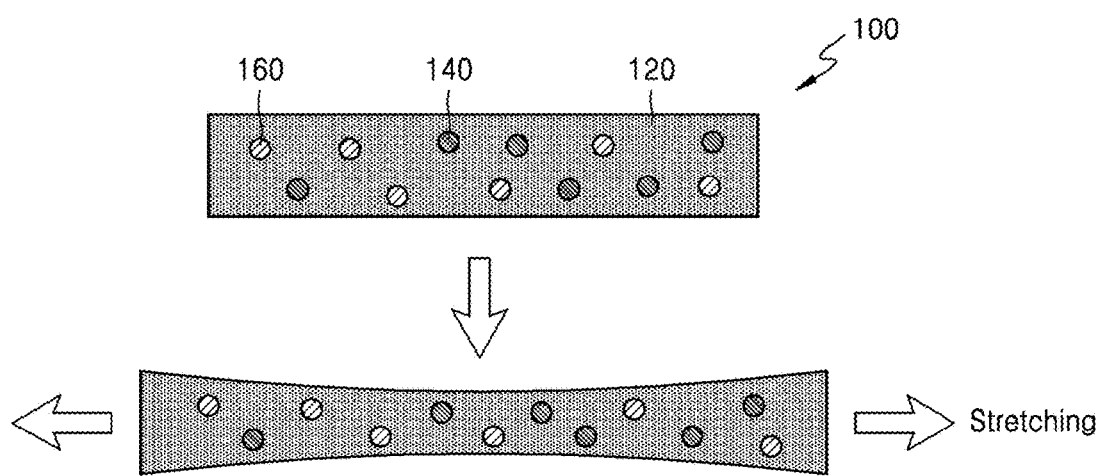
FIG. 1 is a schematic view illustrating a thermoelectric material according to example embodiments.

Example embodiments will now be described more fully with reference to the accompanying drawings, in which some example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference characters and/or numerals in the drawings denote like elements, and thus their description may be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on"). As used herein the term "and/or" includes any and all combinations of one or more of the associated listed items.

It will be understood that, although the terms "first", "second", etc. may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Expressions such as "at least one of," when preceding a list of elements, modify the entire list of elements and do not modify the individual elements of the list.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a schematic view illustrating a thermoelectric material 100 according to example embodiments.

In example embodiments, the thermoelectric material 100 may have high thermoelectric conversion efficiency and stretchability.

In general, the thermoelectric figure of merit (zT) of a thermoelectric material is defined by Equation 1 below:

$$zT=(\alpha^2\sigma T)/\kappa \qquad (1)$$

wherein α denotes a Seebeck coefficient, σ denotes electric conductivity, T denotes absolute temperature, and κ denotes thermal conductivity.

In Equation 1, $\alpha^2\sigma$ is called a power factor.

Referring to Equation 1, the thermoelectric figure of merit (zT) of a thermoelectric material may be increased by increasing the Seebeck coefficient and the electric conductivity of the thermoelectric material and decreasing the thermal conductivity of the thermoelectric material.

As a result of effort to obtain a thermoelectric material having high thermoelectric conversion efficiency and stretchability based on the above-described relation, the thermoelectric material 100 according to example embodiments may be formed by mixing a thermoelectric structure 140 and an electrically conductive material 160 together with a stretchable polymer 120.

The stretchable polymer 120 may be any kind of stretchable polymer. For example, the stretchable polymer 120 may be at least one of poly(styrene-isoprene-styrene) (SIS), poly(styrene-butadiene-styrene) (SBS), poly(styrene-ethylene/butylene-styrene) (SEBS), polyvinylidenefluoride (PVDF), nitrile butadiene rubber (NBR), polyurethane (PU), poly(dimetylsiloxane) (PDMS), polyurethane acrylate (PUA), perfluoropolyether (PFPE), polyester (PE), polytbutadiene (PB), polyisoprene, and a combination thereof.

The thermoelectric structure 140 may be an Sb—Te-containing thermoelectric inorganic material, a Bi—Te-containing thermoelectric inorganic material, a Bi—Sb—Te-containing thermoelectric inorganic material, a Co—Sb-containing thermoelectric inorganic material, a Pb—Te-containing thermoelectric inorganic material, a Ge—Tb-containing thermoelectric inorganic material, a Si—Ge-containing thermoelectric inorganic material, a Sm—Co-containing thermoelectric inorganic material, or a carbon-containing thermoelectric material.

Examples of the Sb—Te-containing thermoelectric inorganic material may include $Sb_2Te_3$, $AgSbTe_2$, and $CuSbTe_2$, and examples of the Bi—Te-containing thermoelectric inorganic material may include $Bi_2Te_3$, and a thermoelectric inorganic material containing $(Bi,Sb)_2(Te,Se)_3$. Examples of the Co—Sb-containing thermoelectric inorganic material may include $CoSb_3$, and examples of the Pb—Te-containing thermoelectric inorganic material may include PbTe and $(PbTe)_mAgSbTe_2$. In addition, any other inorganic material used in the thermoelectric field may be used as the thermoelectric inorganic material 140.

Examples of the carbon-containing material may include carbon nanotubes, graphene, and graphite. In detail, examples of the carbon-containing material may include single walled carbon nanotubes, double walled carbon nanotubes (CNTs), multi-walled carbon nanotubes (MWCNTs), rope carbon nanotubes, graphene oxides, graphene nanoribbons, carbon black, and carbon nanofibers. However, the carbon-containing material is not limited thereto.

The electrically conductive material 160 may be a metallic material or a carbon nanomaterial. Examples of the metallic material may include gold (Au), silver (Ag), platinum (Pt), copper (Cu), nickel (Ni), aluminum (Al), palladium (Pd), rhodium (Rh), and ruthenium (Ru), and examples of the carbon nanomaterial may include carbon nanotubes, graphene, and graphene nanoparticles.

The thermoelectric material 100 may be manufactured by various mixing methods.

For example, the thermoelectric structure 140 and the electrically conductive material 160 may be prepared in the form of powder or flakes and may be dispersed into a solution of the stretchable polymer 120. Thereafter, a solvent may be evaporated from the solution to form the thermoelectric material 100. The solvent may be water or any one selected from various organic solvents. The solvent may be evaporated naturally or by heat.

Alternatively, the thermoelectric material 100 may be manufactured by preparing powder of the stretchable polymer 120, the thermoelectric structure 140, and the electrically conductive material 160, mixing the powder with a solvent, and evaporating the solvent.

Alternatively, a dry mixing method may be used. That is, particles of the stretchable polymer 120, the thermoelectric structure 140, and the electrically conductive material 160 may be mixed together by using a general mixer, and the mixture may be compressed to form the thermoelectric material 100.

Figure 2:
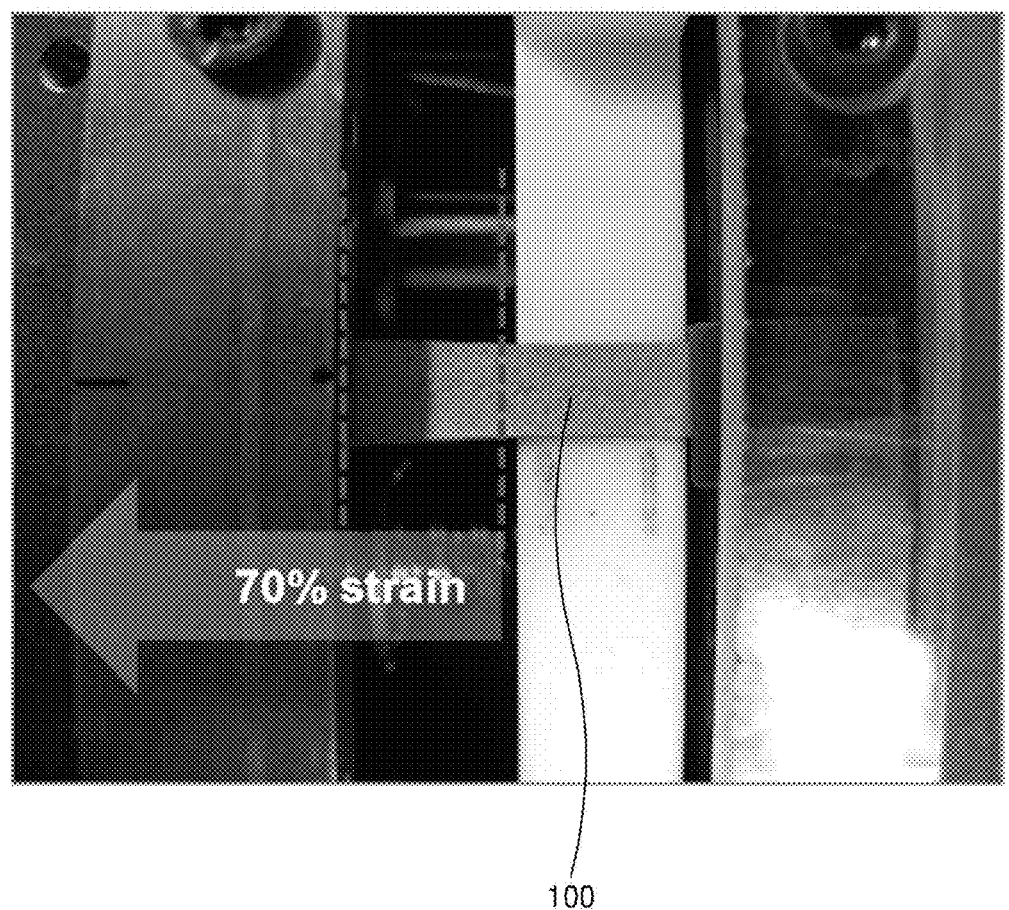
FIG. 2 is an image illustrating a stretched state of a thermoelectric material sample prepared according to example embodiments.
Figure 3:
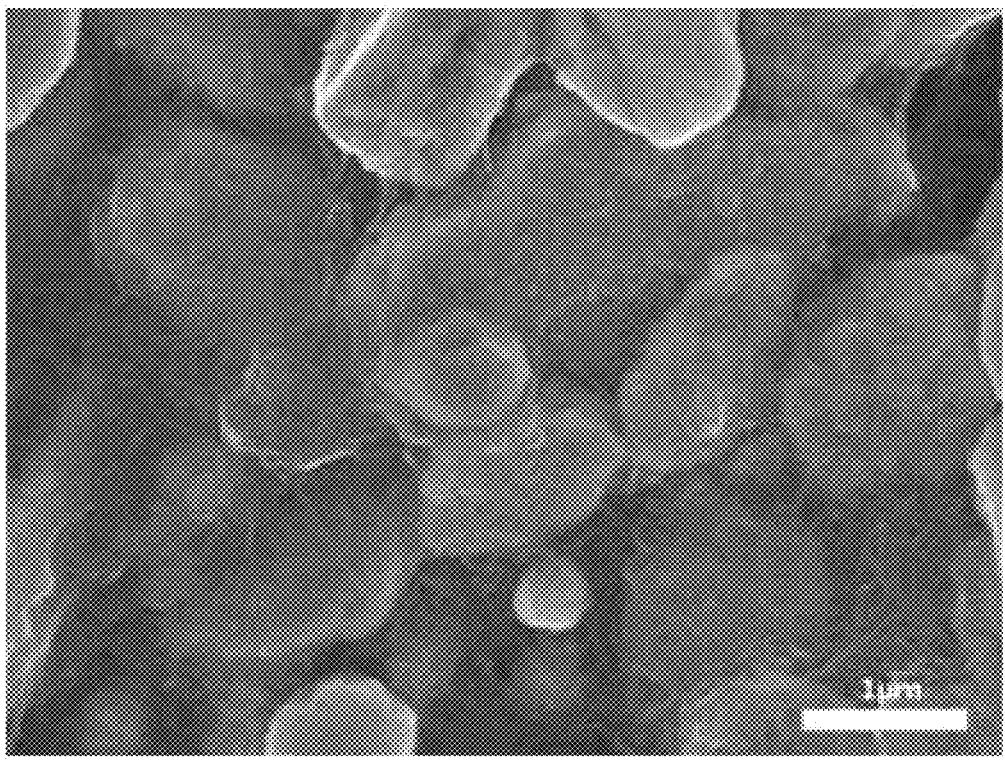
FIG. 3 is a scanning electron microscope (SEM) image taken from a surface of the thermoelectric material sample on an enlarged scale.

FIG. 2 is an image illustrating a stretched state of a sample of the thermoelectric material 100, and FIG. 3 is a scanning electron microscope (SEM) image taken from a surface of the sample on an enlarged scale.

The sample was made by mixing silver (Ag) flakes, carbon nanotubes, and poly(styrene-isoprene-styrene) (SIS), and was stretched by about 70% in a tension test as shown in FIG. 2.

A brief description will now be given of how the sample was made. However, the method described below is a non-limiting example.

First, 2 g of poly(styrene-isoprene-styrene) (SIS) polymer was put into 50 ml of toluene solution and was agitated for about 1 hour while heating the solution at 60° C. to prepare a dispersion solution.

Next, 0.8 g of silver (Ag) flakes and 0.1 g of carbon nanotubes were added to the dispersion solution as an electrically conductive material and a thermoelectric structure, and were mixed for 10 minutes by using a tip sonicator at the power of 700 W.

Thereafter, a dispersion medium was naturally dried at room temperature. In this way, the sample was made in the form of a film.

Figure 4:
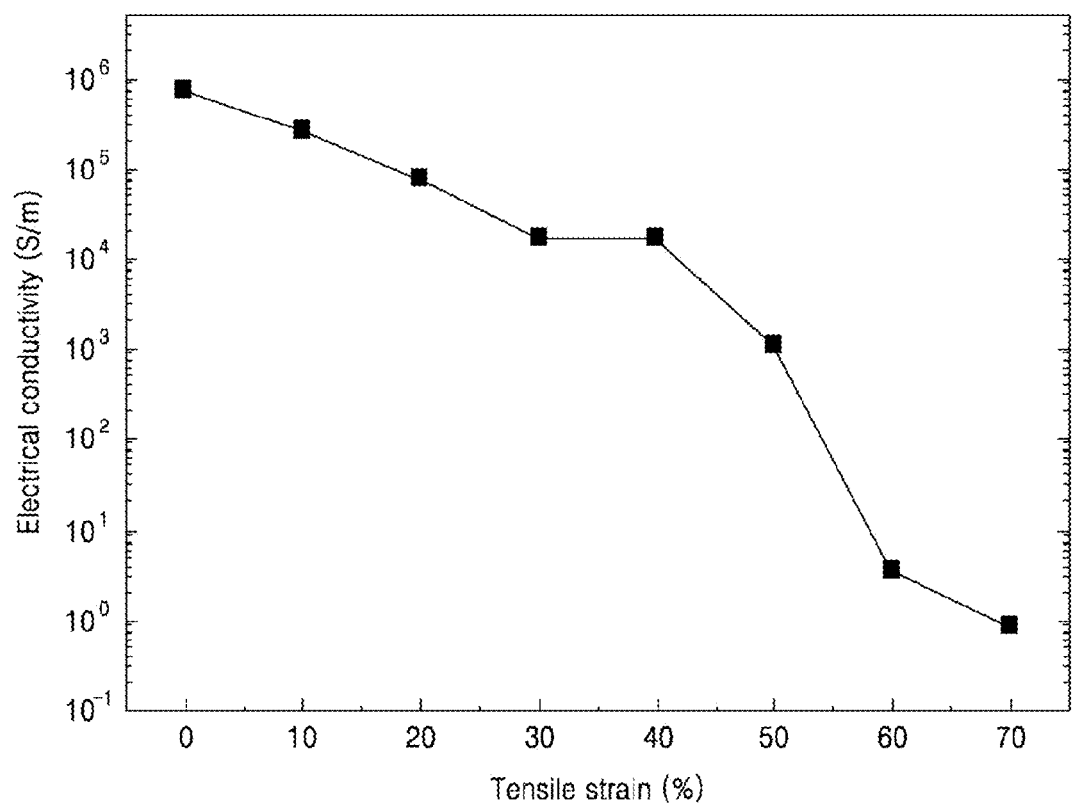
FIG. 4 is a graph illustrating a relationship between electrical conductivity and tensile strain of a thermoelectric material according to example embodiments.
Figure 5:
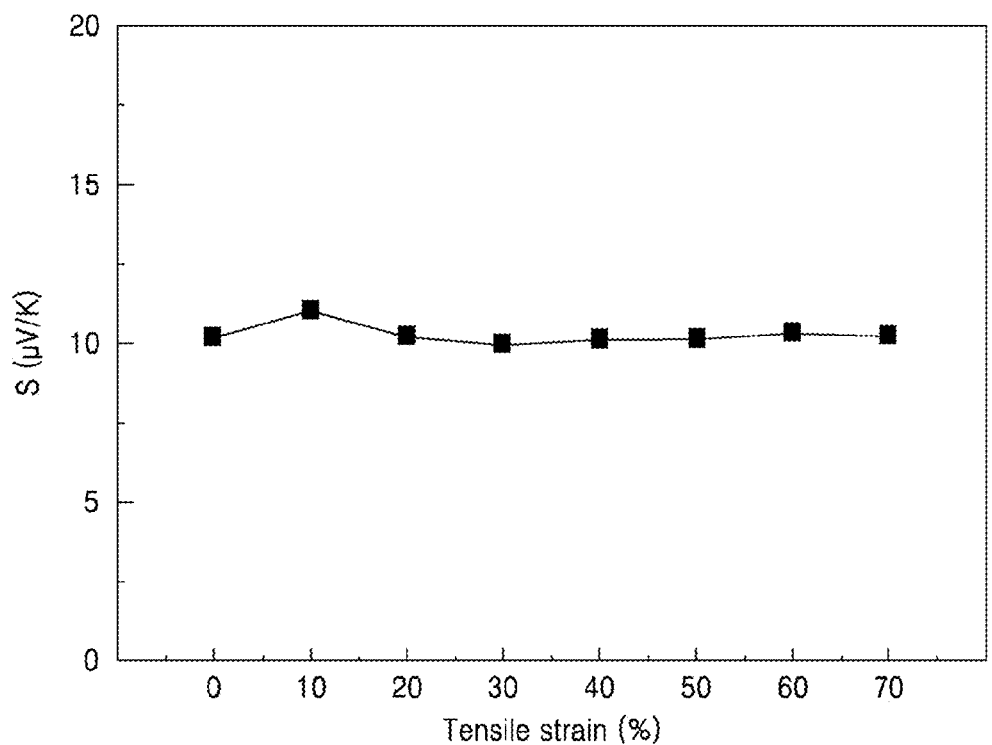
FIG. 5 is a graph illustrating a relationship between a Seebeck coefficient and tensile strain of a thermoelectric material according to example embodiments.
Figure 6:
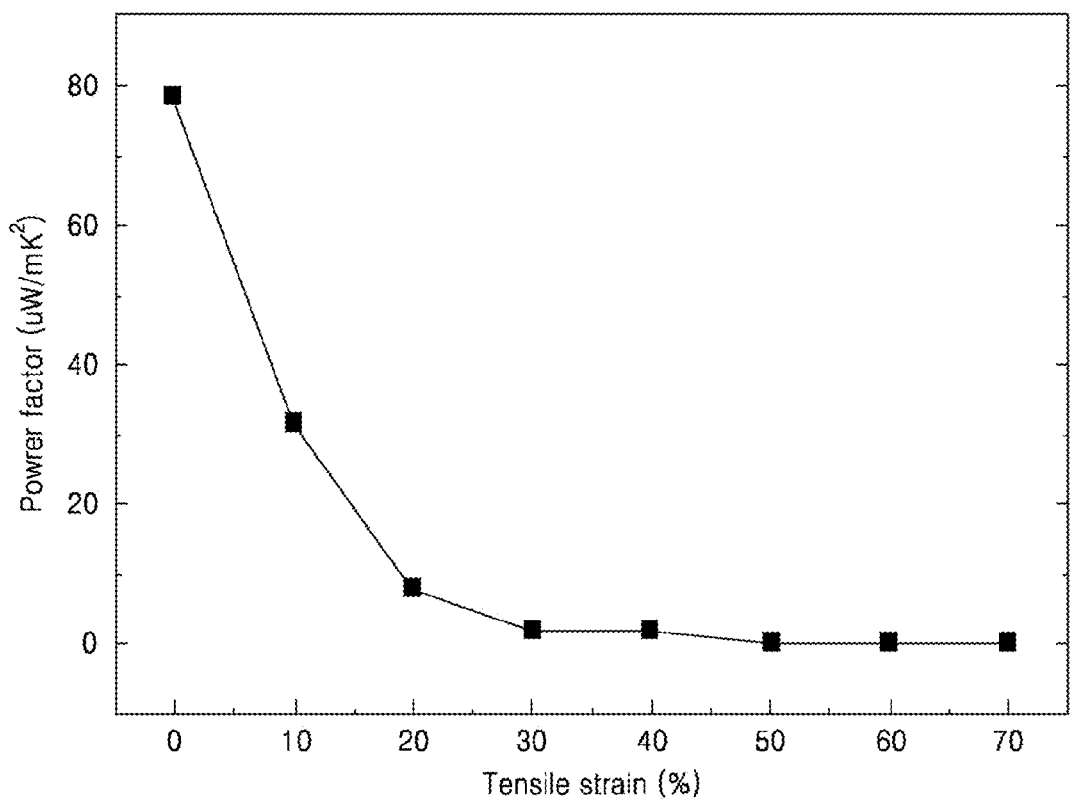
FIG. 6 is a graph illustrating a relationship between a power factor and tensile strain of a thermoelectric material according to example embodiments.

FIGS. 4 to 6 are graphs illustrating the electric conductivity, Seebeck coefficient, and power factor of the thermoelectric material 100 with respect to tensile strain of the thermoelectric material 100 according to example embodiments.

Referring to FIG. 4, the electric conductivity of the thermoelectric material 100 reduces as the tensile strain of the thermoelectric material 100 increases, and the electric conductivity starts to reduce steeply when the tensile strain is about 50% or greater.

Referring to FIG. 5, the Seebeck coefficient of the thermoelectric material 100 is almost constant with respect to the tensile strain of the thermoelectric material 100.

Referring to FIG. 6, the power factor of the thermoelectric material 100 reduces as the tensile strain of the thermoelectric material 100 increases. However, the power factor reduces very little and remains almost constant when the tensile strain is about 20% or greater.

The power factor is $\alpha^2\sigma$ in Equation 1 described above to introduce the thermoelectric figure of merit (zT).

The above-described experimental results may prove that the thermoelectric material 100 could be manufactured to have desired stretchability and thermoelectric efficiency by properly combining components of the thermoelectric material 100.

Hereinafter, thermoelectric materials according to example embodiments will be described.

Figure 7A:
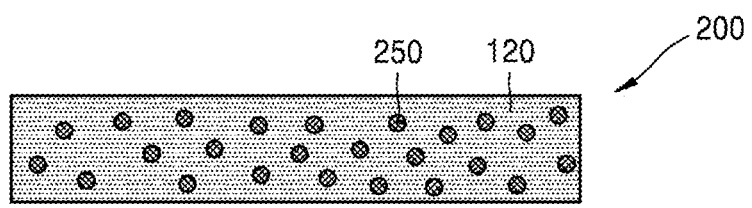
FIG. 7A is a schematic view illustrating a thermoelectric material according to example embodiments.
Figure 8:
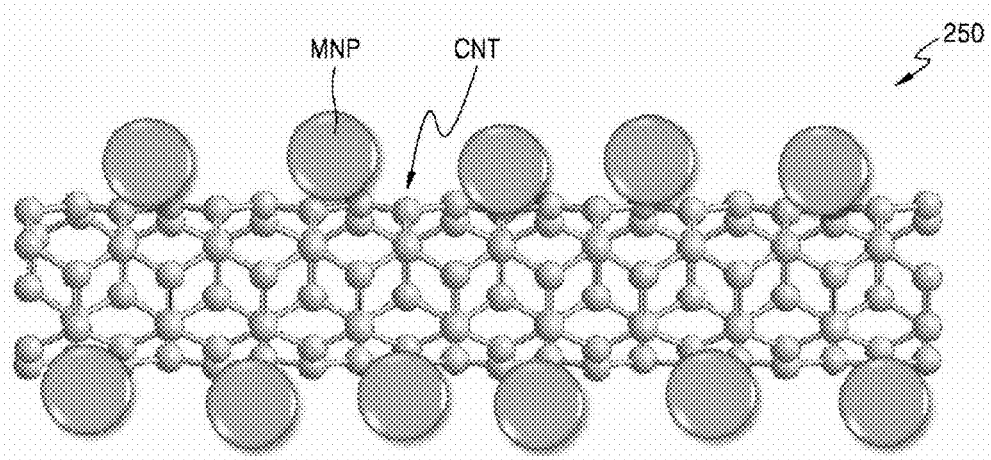
FIG. 8 is a detailed view illustrating a nanostructure included in the thermoelectric material of FIG. 7A.

FIG. 7A is a schematic view illustrating a thermoelectric material 200 according to example embodiments. FIG. 7A is a schematic view illustrating a thermoelectric material 200 according to example embodiments. FIG. 8 is a detailed view illustrating a nanostructure 250 included in the thermoelectric material 200 illustrated in FIG. 7A.

In example embodiments, as shown in FIG. 7A, the thermoelectric material 200 may be made by mixing a stretchable polymer 120 with nanostructures 250 having conductivity and thermoelectric characteristics.

Referring to FIG. 8, each of the nanostructures 250 includes a carbon nanotube CNT and metal nanoparticles MNP adsorbed on the surface of the carbon nanotube.

The carbon nanotubes CNT have thermoelectric characteristics and conductivity, and since the metal nanoparticles MNP are adsorbed on the surfaces of the carbon nanotubes CNT, the nanostructures 250 may have thermoelectric characteristics and high conductivity. Since the thermoelectric material 200 is made by dispersing the nanostructures 250 into the stretchable polymer 120, the thermoelectric material 200 has stretchability.

Figure 7B:
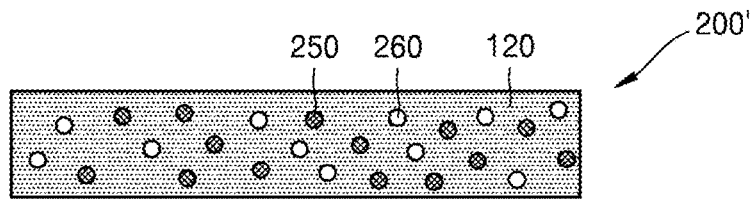
FIG. 7B is a schematic view illustrating a thermoelectric material according to example embodiments.

The nanostructures 250 may be used as the thermoelectric structure 140 of the thermoelectric material 100 illustrated in FIG. 1. That is, the thermoelectric material 100 may be made by mixing the nanostructures 250 and the electrically conductive material 160 with the stretchable polymer 120. In addition, as shown in FIG. 7B, a thermoelectric material 200' according to example embodiments may further include electrically conductive material 260 that is spaced apart from the nanostructures 250. The electrically conductive material 260 may be particles. The electrically conductive material 260 may be may be a metallic material or a carbon nanomaterial. Examples of the metallic material may include gold (Au), silver (Ag), platinum (Pt), copper (Cu), nickel (Ni), aluminum (Al), palladium (Pd), rhodium (Rh), and ruthenium (Ru), and examples of the carbon nanomaterial may include carbon nanotubes, graphene, and graphene nanoparticles. The electrically conductive material 260 may be a different material than the metallic nanoparticle MNP included in the nanostructures 250.

Hereinafter, explanations will be given of the electrical conductivity values, Seebeck coefficients, and power factors of thermoelectric material samples made while varying constitutional components of the samples and contents of the components.

Table 1 below shows thermoelectric properties of samples having different contents of thermoelectric structures and electrically conductive materials.

TABLE 1

| SAMPLE # | COMPOSITION | ELECTRICAL CONDUCTIVITY (S/M) | SEEBECK COEFFICIENT (MV/K) | POWER FACTOR (MW/MK$^2$) |
|---|---|---|---|---|
| 1 | Ag flakes (0.8 g) + CNTs (0.1 g) + SIS polymer (2 g) | 2.449 × 10$^5$ | 10.7 | 28.04 |
| 2 | Ag flakes (0.4 g) + Sb$_2$Te$_3$ (0.4 g) + CNTs (0.1 g) + SIS polymer (2 g) | 3.398 × 10$^2$ | 27.2 | 0.25 |
| 3 | Sb$_2$Te$_3$ (0.4 g) + CNTs (0.1 g) + SIS polymer (2 g) | 1.458 × 10$^2$ | 37.2 | 0.20 |

The samples were made by using SIS polymer as a stretchable polymer, CNTs and/or Sb$_2$Te$_3$ as thermoelectric structures, and silver (Ag) and/or CNTs as electrically conductive materials. That is, CNTs were used as a material having electric conductivity and thermoelectric characteristics. While maintaining the content of the stretchable polymer at a constant value, the contents of the thermoelectric structures and the electrically conductive materials were varied. As a result, the electrical conductivity values of the samples were markedly varied according to the use or content of silver (Ag), and it was analyzed that the power factors of the samples were mainly affected by the use or content of silver (Ag).

Table 2 below shows thermoelectric properties of samples having different contents of thermoelectric structures and electrically conductive materials and the same contents of silver (Ag) flakes and SIS polymer.

TABLE 2

| SAMPLE # | COMPOSITION | ELECTRICAL CONDUCTIVITY (S/M) | SEEBECK COEFFICIENT (MV/K) | POWER FACTOR (MW/MK$^2$) |
|---|---|---|---|---|
| 4 | Ag flakes (0.8 g) + CNTs (0.1 g) + SIS polymer (2 g) | 2.449 × 10$^5$ | 10.7 | 28.04 |
| 5 | Ag flakes (0.8 g) + CNTs (0.05 g) + SIS polymer (2 g) | 5.695 × 10$^5$ | 8.94 | 45.52 |
| 6 | Ag flake (0.8 g) + CNTs (0.025 g) + SIS polymer (2 g) | 7.474 × 10$^5$ | 10.1 | 76.24 |
| 7 | Ag flakes (0.8 g) + Ag/CNTs (0.1 g) + SIS polymer (2 g) | 1.850 × 10$^5$ | 10.3 | 19.63 |

The samples were made by using SIS polymer as a stretchable polymer, CNTs as a thermoelectric structure, and silver (Ag) and CNTs as electrically conductive materials. Ag/CNTs of Sample 7 refers to nanostructures in which silver (Ag) nanoparticles are absorbed on surfaces of CNTs, like the nanostructures 250 of thermoelectric material 200 according to example embodiments that is explained with reference to FIG. 7A. Referring to Table 2, if the content of CNTs is low, the Seebeck coefficient is low but the electric conductivity is high due to a relatively high content of silver (Ag). As a result, the power factor is high.

Figure 9A:
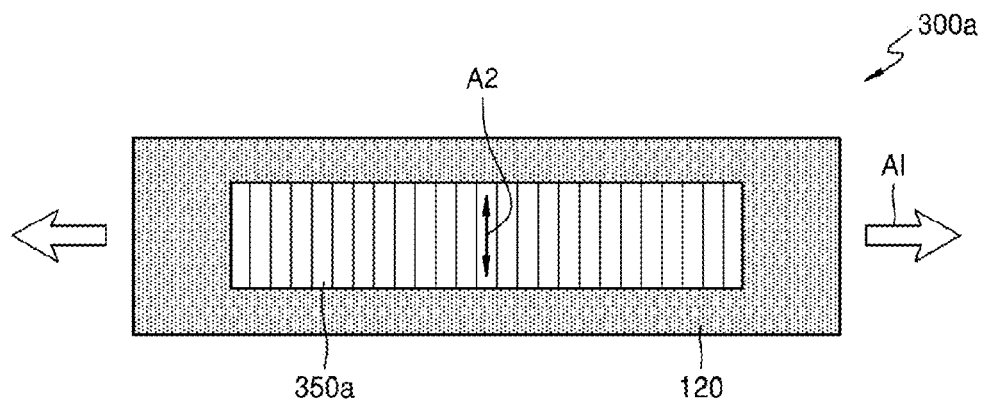
FIGS. 9A to 9C are schematic views illustrating thermoelectric materials according to example embodiments.
Figure 9B:
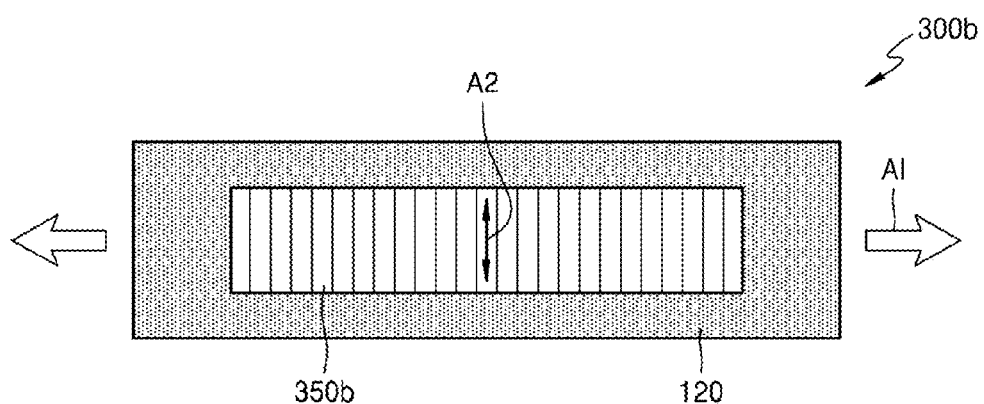
Figure 9C:
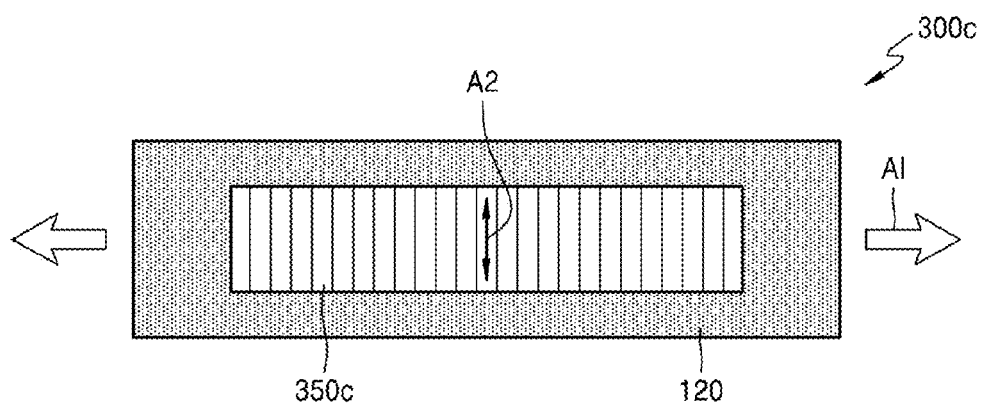

FIGS. 9A to 9C are schematic views illustrating thermoelectric materials 300a to 300c according to example embodiments.

Referring to FIG. 9A, the thermoelectric material 300a includes carbon nanotubes having thermoelectric characteristics and electric conductivity. In detail, the thermoelectric material 300a includes a stretchable polymer 120 and a multi-walled carbon nanotube array 350a.

In the multi-walled carbon nanotube array 350a, carbon nanotubes may be arranged in one direction. That is, lengths of a plurality of nanotubes constituting the multi-walled carbon nanotube array 350a may be parallel to each other. The multi-walled carbon nanotube array 350a may be embedded in the stretchable polymer 120. The stretchable polymer 120 may have uniaxial stretchability as indicated by an arrow A1. In other words, a stretching direction of the stretchable polymer 120 may be indicated by the arrow A1. A length direction A2 of the carbon nanotubes of the multi-walled carbon nanotube array 350a and a stretchable direction A1 of the stretchable polymer 120 may be perpendicular to each other.

Referring to FIG. 9B, the thermoelectric material 300b includes carbon nanostructures having thermoelectric characteristics and electric conductivity. In detail, the thermoelectric material 300b includes a stretchable polymer 120 and a nanostructure array 350b. The nanostructures in the nanostructure array 350b may include multi-walled carbon nanotubes with metal nanoparticles adsorbed on the surfaces of the carbon nanotubes (e.g., multi-walled carbon nanotubes), such as a plurality of the nanostructures 250 described previously with reference to FIG. 8.

In the nanostructure array 350b, the carbon nanotubes of the nanostructures in the nanostructure array 350b may be arranged in one direction. That is, lengths of nanotubes in the nanostructures constituting the nanostructure array 350b may be parallel to each other. The nanostructure array 350b may be embedded in the stretchable polymer 120. The stretchable polymer 120 may have uniaxial stretchability as indicated by an arrow A1. A length direction A2 of the carbon nanotubes in the nanostructures of the nanostructure array 350b and a stretchable direction A1 of the stretchable polymer 120 may be perpendicular to each other.

Referring to FIG. 9C, the thermoelectric material 300c may be the same as the thermoelectric material 300b described in FIG. 9B, except the nanostructure array 350c further includes additional electrically conductive material dispersed in the stretchable polymer 120 and separate from the nanostructure array 350c, similar to the electrically conductive material 260 described in FIG. 7B.

Although examples are described with reference to FIGS. 9A to 9C where the carbon nanotube arrays 350a to 350c may include multi-walled carbon nanotubes, example embodiments are not limited thereto. For example, single-walled carbon nanotubes or a different carbon-containing structure (e.g., rope carbon nanotubes) may be used instead of multi-walled carbon nanotubes.

Figure 10A:
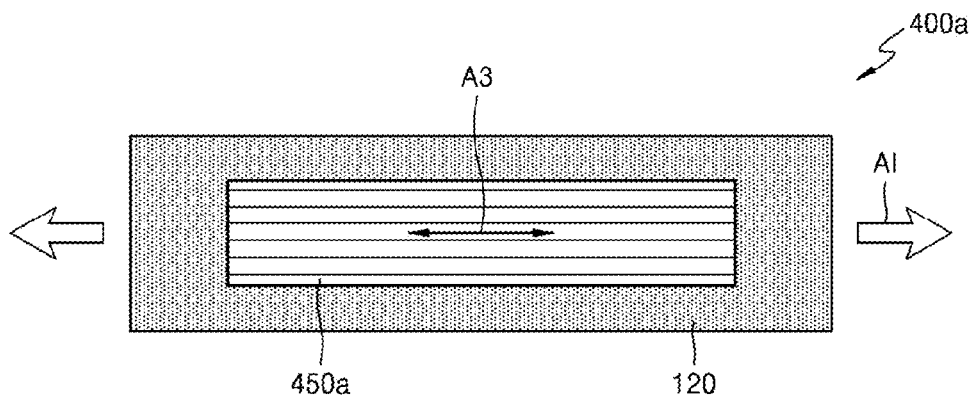
FIGS. 10A to 10C is are schematic views illustrating thermoelectric materials according to example embodiments.
Figure 10B:
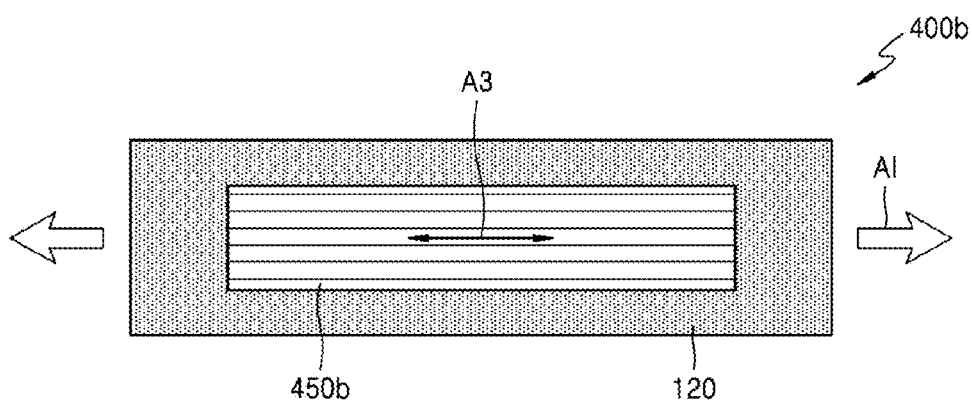
Figure 10C:
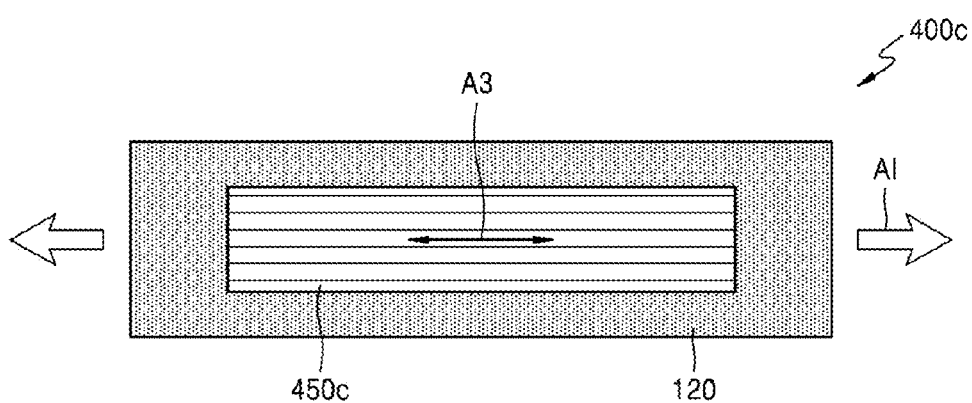

FIGS. 10A to 10C are schematic views illustrating thermoelectric materials 400a, 400b, and 400c according to example embodiments.

Referring to FIG. 10A, the thermoelectric material 400a may have a structure that is similar to the thermoelectric material 300a of FIG. 9A, except for an arrangement of the carbon nanotubes in the multi-walled carbon nanotube array 450a compared to the carbon nanotubes in the multi-walled carbon nanotube array 350a. That is, in the thermoelectric material 400a, a multi-walled carbon nanotube array 450a in which carbon nanotubes are arranged in one direction is embedded in a stretchable polymer 120 having uniaxial stretchability (A1). In the thermoelectric material 400a, a length direction A3 of the multi-walled carbon nanotube array 450a may be parallel to a stretchable direction A1. In other words, a length direction A3 of the carbon nanotubes in the multi-walled carbon nanotube array 450a may be parallel to a stretching direction of the stretchable polymer 120.

Referring to FIG. 10B, the thermoelectric material 400b may have a structure that is similar to the thermoelectric material 300b of FIG. 9B, except for an arrangement of the carbon nanotubes in the nanostructure array 450b compared the carbon nanotubes in the nanostructure array 350b. That is, in the thermoelectric material 400b, a nanostructure array 450b in which carbon nanotubes are arranged in one direction is embedded in a stretchable polymer 120 having uniaxial stretchability (A1). In the thermoelectric material 400b, a length direction A3 of the carbon nanotubes in the nanostructure array 450b may be parallel to a stretchable direction A1. In other words, a length direction A3 of the carbon nanotubes in the nanostructure array 450b may be parallel to a stretching direction of the stretchable polymer 120.

Referring to FIG. 10C, the thermoelectric material 400c may have a structure that is the same as the thermoelectric material 400b in FIG. 10B, except that the nanostructure array 450c further includes additional electrically conductive material dispersed in the stretchable polymer and separate from the nanostructure array 450c, similar to the electrically conductive material 260 described in FIG. 7B.

The above-described thermoelectric materials 100, 200, 200', 300a, 300b, 300c, 400a, 400b, and 400c may further include electrode structures to provide a current for inducing thermoelectric conversion therein or to use or collect electricity generated by thermoelectric conversion therein. Each of the electrode structures may include two electrodes disposed on and electrically connected to both ends of each of the thermoelectric materials 100, 200, 200', 300a, 300b, 300c, 400a, 400b, and 400c. The thermoelectric materials 100, 200, 200', 300a, 300b, 300c, 400a, 400b, and 400c, and electronic devices such as power consuming devices, power storage devices, or power supply devices connected to the electrodes may be used as thermoelectric devices having various functions.

Figure 11:
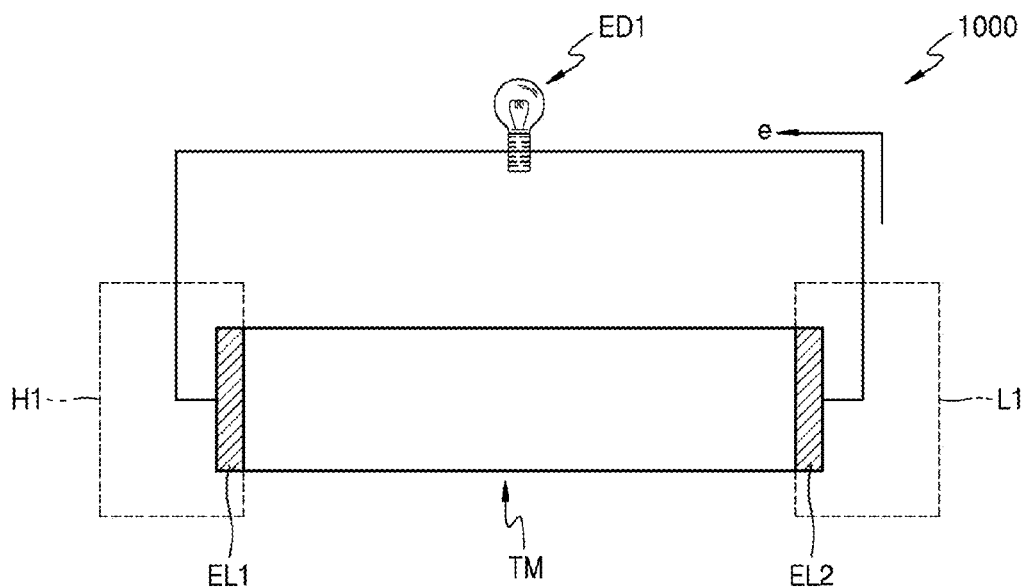
FIG. 11 is a schematic view illustrating a thermoelectric device according to example embodiments.

FIG. 11 is a schematic view illustrating a thermoelectric device 1000 according to example embodiments.

The thermoelectric device 1000 includes a thermoelectric material TM, first and second electrodes EL1 and EL2 formed at respective both ends of the thermoelectric material TM, and a power consuming device ED1 disposed between the first and second electrodes EL1 and EL2.

An end of the thermoelectric material TM (for example, where the first electrode EL1 is formed) may be in contact with a relatively high temperature region H1, and the other end of the thermoelectric material TM (for example, where the second electrode EL2 is formed) may be in contact with a relatively low temperature region L1. In this case, electricity may be generated in the thermoelectric material TM by the thermoelectric effect. For example, electrons $e^-$ (or holes) may move from the end of the thermoelectric material TM making contact with the high temperature region H1 to the other end of the thermoelectric material making contact with the low temperature region L1. The electrons $e^-$ (or holes) may flow through the power consuming device ED1. In this way, electricity generated by the thermoelectric material TM may be consumed by the power consuming device ED1.

A bulb is shown as the power consuming device ED1. However, the bulb is a non-limited example. That is, various kinds of loads consuming electricity generated by the thermoelectric material TM may be used.

The thermoelectric material TM may be any one of the above-described thermoelectric materials 100, 200, 200', 300a, 300b, 300c, 400a, 400b, and 400c or may be a combination thereof. Since the thermoelectric material TM has stretchability and improved thermoelectric characteristics, the thermoelectric device 1000 may have high thermoelectric conversion efficiency.

Figure 12:
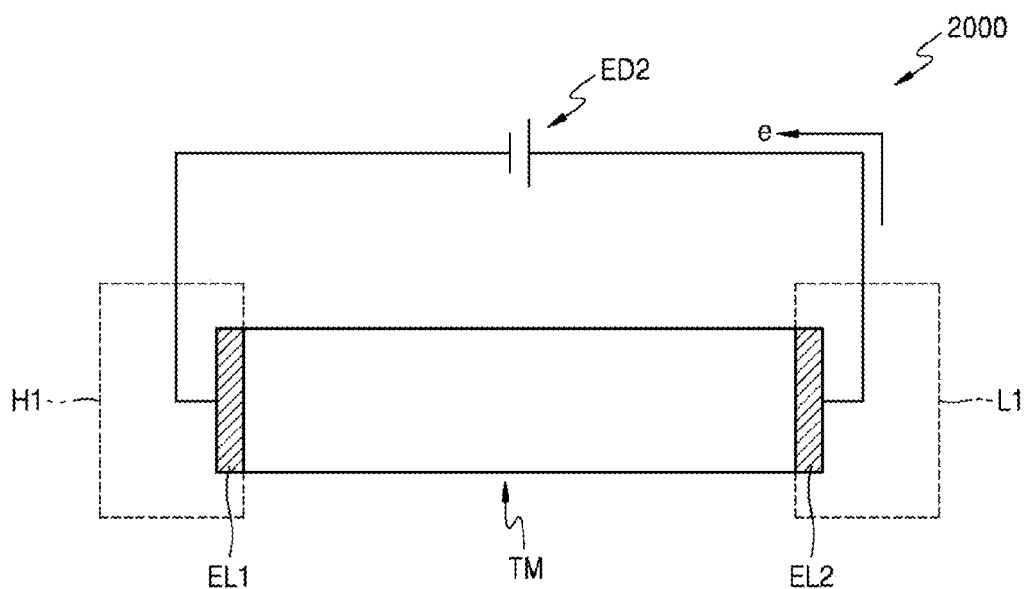
FIG. 12 is a schematic view illustrating a thermoelectric device according to example embodiments.

FIG. 12 is a schematic view illustrating a thermoelectric device 2000 according to example embodiments.

The thermoelectric device 2000 is different from the thermoelectric device 1000 of FIG. 11, in that an electronic device connected to both ends of the thermoelectric device 2000 is a power storage device ED2. For example, the power storage device ED2 may be a storage battery configured to store electricity generated by a thermoelectric material TM of the thermoelectric device 2000.

Figure 13:
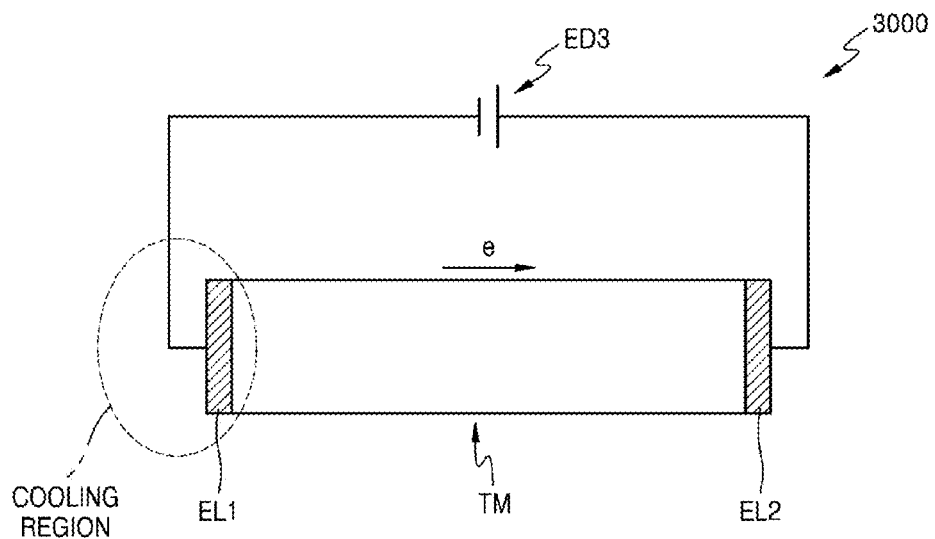
FIG. 13 is a schematic view illustrating a thermoelectric device according to example embodiments.

FIG. 13 is a schematic view illustrating a thermoelectric device 3000 according to example embodiments.

The thermoelectric device 3000 may be a thermoelectric cooling device.

Referring to FIG. 13, first and second electrodes EL1 and EL2 may be provided on both ends of a thermoelectric material TM, and a power supply device ED3 may be connected between the first and second electrodes EL1 and EL2. If a current is supplied from the power supply device ED3 to the thermoelectric material TM, an end of the thermoelectric material TM may absorb heat from surrounding objects by the Peltier effect. That is, heat may be absorbed at an end of the thermoelectric material TM. Therefore, the surrounding area of the end of the thermoelectric material TM may be cooled. The structure of the power supply device ED3 may be variously changed.

The thermoelectric device 3000 may be used for various electronic apparatuses requiring hot spot cooling. For example, the thermoelectric device 3000 may be applied to portable electronic apparatuses such as smartphones, tablet personal computers (PCs), or micro packages, or may be applied to wearable small electronic apparatuses.

Each of the thermoelectric materials TM of the thermoelectric devices 1000, 2000, and 3000 described with reference to FIGS. 11 to 13 may be one selected from the above-described thermoelectric materials 100, 200, 200', 300a, 300b, 300c, 400a, 400b, and 400c according to example embodiments, and combinations thereof.

In FIGS. 11 to 13, electrode structures of the thermoelectric devices 1000, 2000, and 3000 are plate-shaped. However, the electrode structures may have other shapes such as wire shapes. If the thermoelectric materials 300 and 400 of FIGS. 9 and 10 in which the multi-walled carbon nanotube arrays 350 and 450 are embedded in the stretchable polymers 120 are used as the thermoelectric materials TM of the thermoelectric devices 1000, 2000, and 3000, wire structures may be further used to electrically expose the multi-walled carbon nanotube arrays 350 and 450 to the outsides of the stretchable polymers 120 and to thus electrically connect the first and second electrodes EL1 and EL2 to the multi-walled carbon nanotube arrays 350 and 450. For example, the thermoelectric materials 300 and 400 may be manufactured by forming wires to be exposed to the outsides on the multi-walled carbon nanotube arrays 350 and 450 using a material such as metal flakes, and then embedding the multi-walled carbon nanotube arrays 350 and 450 in the stretchable polymers 120.

Since the thermoelectric devices 1000, 2000, and 3000 according to example embodiments include the thermoelectric materials TM having stretchability, the thermoelectric devices 1000, 2000, and 3000 may easily be applied to wearable apparatuses such as self-power generating wearable apparatuses.

Figure 14:
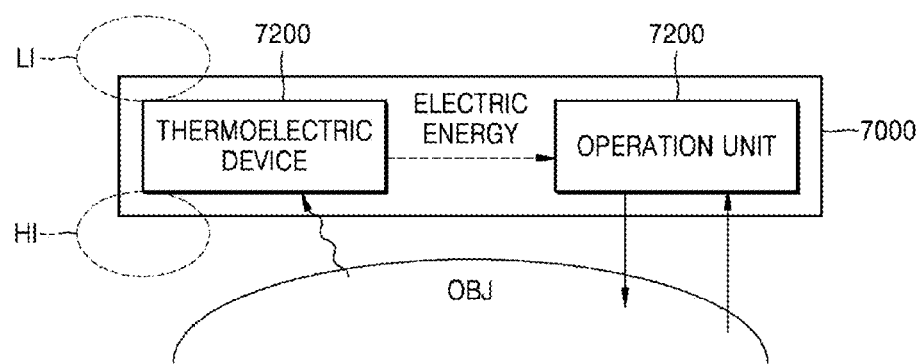
FIG. 14 is a schematic block diagram of a wearable electronic apparatus according to example embodiments.

FIG. 14 is a schematic block diagram of a wearable electronic apparatus 7000 according to example embodiments.

The wearable electronic apparatus 7000 may be put on an object OBJ for detecting states of the object OBJ. The wearable electronic apparatus 7000 includes a thermoelectric device 7200 and an operation unit 7400.

The thermoelectric device 7200 includes one of the above-described thermoelectric materials according to example embodiments, and a power storage device such as the power storage device ED2 shown in FIG. 12 for storing electricity generated by the thermoelectric material.

The thermoelectric device 7200 may function as a self-power generating device capable of converting thermal energy TE of the object OBJ into electricity. That is, due to thermal energy provided by the object OBJ, a temperature difference is generated between adjacent and far regions of the thermoelectric device 7200 relative to the object OBJ, and thus electricity is generated in the thermoelectric device 7200 having a temperature gradient. Then, electric energy is stored in the thermoelectric device 7200.

The operation unit 7400 may inspect the object OBJ by using electric energy received from the thermoelectric device 7200. For example, the operation unit 7400 may send an input signal S1 to the object OBJ and may receive an output signal S2 generated from the input signal S1 as a result of interaction with the object OBJ. For example, the input signal S1 may be light or ultrasonic waves, and the output signal S2 may be light or ultrasonic waves modified by interaction with the object OBJ and thus having properties different from those of the input signal S1.

The operation unit 7400 may be used to inspect the health or motion of the object OBJ. For example, the operation unit 7400 may include a light source or ultrasonic device for generating input signals S1. In addition, the operation unit 7400 may include one or more of various sensors for receiving output signals S2. For example, the operation unit 7400 may include an optical sensor, an ultrasonic sensor, a pressure sensor, or a strain sensor.

The operation unit 7400 may be controlled in a wired or wireless manner. For example, the operation unit 7400 may be an element of a remote medical examination system capable of measuring the health status of the object OBJ.

The above-described wearable electronic apparatus 7000 is a non-limiting example. That is, various modifications or changes may be made. For example, any kind of wearable apparatus including a thermoelectric device as a self-power generating device may be provided. For example, example embodiments may provide electronic goggles, watches, or clothes capable of generating electricity from a temperature difference between a human body and the surroundings and using the electricity as operation energy. In addition, example embodiments may provide military uniforms equipped with such wearable electronic apparatuses.

As described above, according to example embodiments, thermoelectric materials may have stretchability and high thermoelectric efficiency.

Therefore, the thermoelectric materials may be used in the manufacture of thermoelectric devices having high thermoelectric conversion efficiency, together with power consuming devices, power storage devices, or power supply devices.

The thermoelectric devices may be applied to self-power generating wearable electronic apparatuses or other various electronic apparatuses requiring hot spot cooling.

It should be understood that the example embodiments described herein should be considered in a descriptive sense only and not for purposes of limitation. Descriptions of features or aspects within each thermoelectric material and/or device according to example embodiments should typically be considered as available for other similar features or aspects in other thermoelectric materials and/or devices according to example embodiments.

While some example embodiments have been described with reference to the figures, it will be understood by those of ordinary skill in the art that various changes in form and details may be made therein without departing from the spirit and scope of the following claims.

What is claimed is:

1. A thermoelectric material, comprising:
    a stretchable polymer; and
    a thermoelectric structure and electrically conductive material that are mixed together in the stretchable polymer, the thermoelectric structure including a carbon-containing material, wherein
    the carbon-containing material includes carbon nanotubes,
    the carbon nanotubes are arranged in an array, and
    lengths of the carbon nanotubes are parallel to each other.

2. The thermoelectric material of claim 1, wherein the stretchable polymer includes at least one of poly(styrene-isoprene-styrene) (SIS), poly(styrene-butadiene-styrene) (SBS), poly(styrene-ethylene/butylene-styrene) (SEBS), polyvinylidenefluoride (PVDF), nitrile butadiene rubber (NBR), polyurethane (PU), poly(dimetylsiloxane) (PDMS), polyurethane acrylate (PUA), perfluoropolyether (PFPE), polyester (PE), polybutadiene (PB), and polyisoprene.

3. The thermoelectric material of claim 1, wherein the electrically conductive material includes metal nanoparticles.

4. The thermoelectric material of claim 3, wherein
    the carbon nanotubes embedded in the stretchable polymer, and
    the metal nanoparticles are adsorbed on the carbon nanotubes.

5. The thermoelectric material of claim 1, wherein the electrically conductive material includes at least one of a carbon nanomaterial and a metallic material.

6. The thermoelectric material of claim 5, wherein the metallic material includes at least one of gold (Au), silver (Ag), platinum (Pt), copper (Cu), nickel (Ni), aluminum (Al), palladium (Pd), rhodium (Rh), and ruthenium (Ru).

7. The thermoelectric material of claim 1, wherein
    the stretchable polymer has uniaxial stretchability in a first direction that corresponds to a length of the stretchable polymer, and
    the first direction crosses a direction of the lengths of the carbon nanotubes.

8. The thermoelectric material of claim 1, wherein the stretchable polymer includes at least one of poly(styrene-isoprene-styrene) (SIS), poly(styrene-butadiene-styrene) (SBS), poly(styrene-ethylene/butylene-styrene) (SEBS), polyvinylidenefluoride (PVDF), nitrile butadiene rubber (NBR), polyurethane (PU), polyurethane acrylate (PUA), perfluoropolyether (PFPE), polybutadiene (PB), and polyisoprene.

* * * * *